United States Patent [19]

Rohe et al.

[11] 4,080,193
[45] Mar. 21, 1978

[54] (TRIFLUOROMETHYLPHENOXY)-PHENYLUREA COMPOUNDS AND HERBICIDAL COMPOSITIONS

[75] Inventors: Lothar Rohe, Wuppertal; Jürgen Schramm, Dormagen; Ludwig Eue; Robert Rudolf Schmidt, both of Cologne, all of Germany

[73] Assignee: Bayer Aktiengesellschaft, Leverkusen, Germany

[21] Appl. No.: 555,515

[22] Filed: Mar. 5, 1975

[30] Foreign Application Priority Data

Mar. 9, 1974 Germany .............................. 2411320

[51] Int. Cl.$^2$ ........................ A01N 9/20; C07C 127/19
[52] U.S. Cl. .................................. 71/120; 260/553 A
[58] Field of Search ...................... 260/553 A; 71/120

[56] References Cited

U.S. PATENT DOCUMENTS

| 3,060,235 | 10/1962 | Martin et al. | 260/553 A |
| 3,165,549 | 1/1965 | Martin et al. | 71/120 |
| 3,177,249 | 4/1965 | Martin et al. | 71/120 |
| 3,901,687 | 8/1975 | Bailey | 71/120 |

*Primary Examiner*—Glennon H. Hollrah
*Attorney, Agent, or Firm*—Burgess, Dinklage & Sprung

[57] ABSTRACT

New (trifluoromethylphenoxy)-phenylureas of the formula:

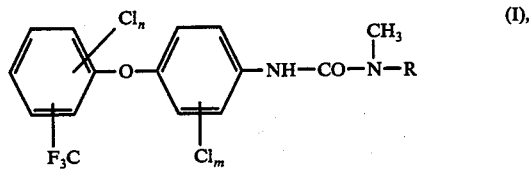

wherein
R is hydrogen or methyl and
n and m, which may be identical or different, are each 0, 1, 2, 3 or 4, but only n and m may be 0 if the trifluoromethyl group is in the 3-position and have strong herbicidal properties.

21 Claims, No Drawings

(TRIFLUOROMETHYLPHENOXY)-PHENYLUREA COMPOUNDS AND HERBICIDAL COMPOSITIONS

The present invention relates to certain new (trifluoromethylphenoxy)-phenylurea compounds and to herbicidal compositions containing them.

It is known from German Auslegeschrift (German Published Specification) No. 1,142,251 that N,N-dimethyl-N'-[4-(4-chlorophenoxy)-phenyl]-urea can be used for combating weeds. However, this compound is not active against all weeds, especially if low amounts and low concentrations are used; for example, it has a low activity against monocotyledons, for example Poa and Digitaria.

The present invention provides, as new compounds, the (trifluoromethylphenoxy)-phenylureas of the general formula:

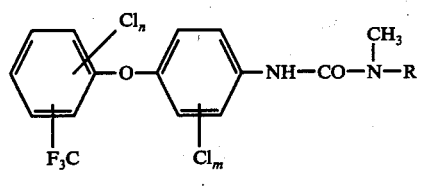

wherein
R is hydrogen or methyl and
n and m, which may be identical or different, are each 0, 1, 2, 3 or 4, but only n or m may be 0 if the trifluoromethyl group is in the 3-position.

The compounds of this invention have been found to display strong herbicidal properties.

Preferably n i 0, 1 or 2 and m is 0 or 1.

Surprisingly, the (trifluoromethylphenoxy)-phenylureas according to the invention display a substantially greater herbicidal action than the nearest compound previously known from the state of the art, namely N,N-dimethyl-N'-[4-(4-chlorophenoxy)-phenyl]-urea. The compounds according to the invention are markedly more active against weeds, for example Poa annua and Digitaria spec., and furthermore their good toleration, above all in carrots, should be singled out. The compounds according to the invention thus represent an enrichment of the art.

The invention also provides a process for the preparation of a (trifluoromethylphenoxy)-phenylurea of the formula (I) in which:

(a) a (trifluoromethylphenoxy)-aniline of the general formula:

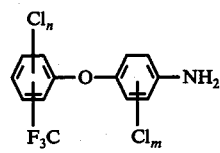

wherein
n and m have the above-mentioned meanings, is reacted with phosgene and subsequently, optionally without intermediate isolation thereof, the isocyanate produced is reacted with an amine of the general formula:

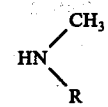

wherein
R has the above-mentioned meaning, optionally in the presence of a solvent, or (b) a (trifluoromethylphenoxy)-aniline of the formula (II) above is reacted with N,N-dimethylcarbamic acid chloride of the formula:

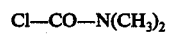

optionally in the presence of an acid acceptor and optionally in the presence of a solvent, or (c) a (trifluoromethylphenoxy)-aniline of the formula (II) above is reacted with methylisocyanate of the formula:

optionally in the presence of a solvent.

In process variant (b) only those compounds of the formula (I) wherein R is methyl are obtained, whereas in process variant (c) only those compounds of the formula (I) wherein R is hydrogen are obtained.

If 4-(3-trifluoromethyl-4-chlorophenoxy)-aniline, phosgene and monomethylamine are used as starting materials according to process variant (a), 4-(4-trifluoromethyl-phenoxy)-aniline and N,N-dimethyl-carbamic acid chloride are used as starting materials according to process variant (b) and 4-(2-trifluoromethyl-4-chloro-phenoxy)-aniline and methylisocyanate are used as starting materials according to process variant (c), the course of the reactions can be represented by the following equations:

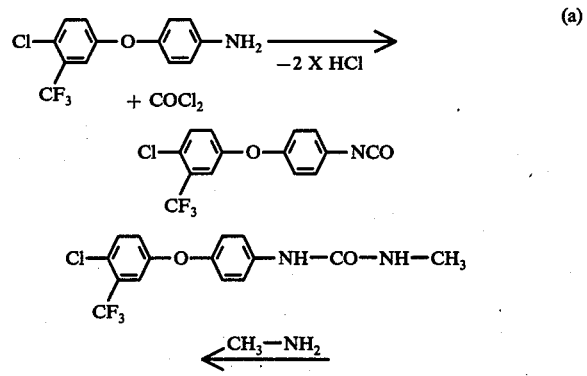

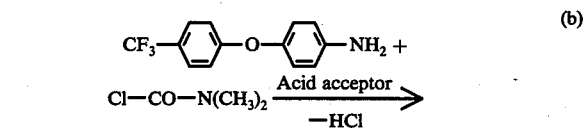

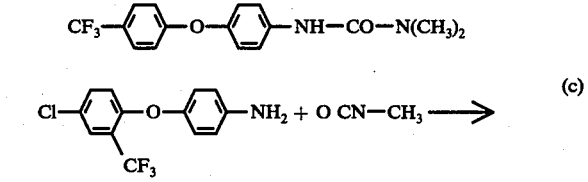

-continued

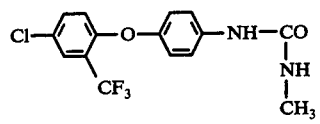

The (trifluoromethylphenoxy)-anilines of the formula (II) are new but can be prepared according to generally customary methods which are described in the literature, for example from substituted aminophenols by means of trifluoromethylhalogenobenzenes (reference may be made to the detailed information thereon, given in the preparative Examples).

The phosgene and the amines (III) required for process variant (a) are known from the literature and can be prepared according to generally customary methods, even on an industrial scale.

N,N-dimethylcarbamic acid chloride to be used as a starting material in the process variant (b) and the methylisocyanate to be used according to process variant (c) are both known from the literature and can be prepared according to generally customary methods.

All three process variants (a), (b) and (c) are preferably carried out in the presence of suitable solvents or diluents. Practically all inert organic solvents can be used for this purpose, especially aliphatic and aromatic, optionally chlorinated, hydrocarbons, such as benzenes, toluene, xylene, benzine, methylene chloride, chlorogorm, carbon tetrachloride and chlorobenzene; ethers, for example diethyl ether, dibutyl ether and dioxan; ketones, for example acetone, methyl ethyl ketone, methyl isopropyl ketone and methyl isobutyl ketone; nitriles, such as acetonitrile and propionitrile; and amines, such as pyridine.

All customary acid-binding agents can be used as acid acceptors in process variant (b). Alkali metal carbonates and alkali metal alcoholates, such as sodium carbonate and potassium carbonate, have proved particularly suitable, as have aliphatic, aromatic or heterocyclic tertiary amines, for example triethylamine, dimethylaniline, dimethylbenzlamine and pyridine.

The reaction temperatures can be varied within a fairly wide range. In general, the reaction is carried out at between $-10°$ and $150°$ C, preferably at from $-5°$ to $130°$ C in process variant (a), at from $0°$ to $80°$ C in process variant (b) and at from $0°$ to $40°$ C in process variant (c).

To carry out the process variant (a), the phosgene and the amine are in general employed in excess. In order to remove excess phosgene after the reaction, nitrogen is passed over the reaction mixture, the amine is then added dropwise and the reaction mixture is worked up by the method customary in the laboratory. To carry out process variant (b), the N,N-dimethylcarbamic acid chloride is in most cases employed in up to 40% excess, and in process variant (c) the methylisocyanate is generally employed in up to 30% excess. In both process variants, the working up is carried out in accordance with methods customary in the laboratory.

The following examples are given for the purpose of illustrating the preparation of the compounds used in the present invention:

EXAMPLE 1

Preparation of N,N-dimethyl-N'-[3-chloro-4-(3-trifluoromethyl-phenoxy)-phenyl]-urea

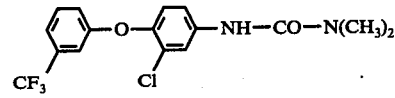 (1)

Phosgene was introduced into 20.1 g (0.07 mole) of 3-chloro-4-(3-trifluoromethyl-phenoxy)-aniline, dissolved in 200 ml of chlorobenzene, at $-5°$ C for 1 hour. The reaction mixture was then warmed slowly and the introduction of phosgene was repeated at $120°$ C until the reaction mixture had become a clear solution. Nitrogen was then passed over it for half an hour to remove remnants of phosgene; dimethylamine was then introduced at $0°$ C until the reaction mixture showed a basic reaction. After stirring for one hour at room temperature, the bulk of the chlorobenzene was distilled off and the residue was recrystallized from a little acetonitrile.

16 g (65% of theory) of N,N-dimethyl-N'-[3-chloro-4-(3-trifluoromethyl-phenoxy)phenyl]-urea were obtained in the form of white crystals of melting point $166°$ C.

The following compounds were obtained analogously to Example 1 in accordance with process variant (a):

Table

| Ex. No. | Structural formula | Melting point (° C) |
|---|---|---|
| 2 | (CF₃, Cl, Cl)—O—⟨⟩—NH—CO—N(CH₃)₂ | 173 |
| 3 | (Cl, CF₃)—O—⟨⟩—NH—CO—N(CH₃)₂ | 152 |
| 4 | (CF₃)—O—⟨⟩—NH—CO—N(CH₃)₂ | 130 |
| 5 | (CF₃, Cl)—O—(Cl)⟨⟩—NH—CO—N(CH₃)₂ | 173 |
| 6 | (CF₃, Cl)—O—(Cl)⟨⟩—NH—CO—N(CH₃)₂ | 178-180 |
| 7 | (Cl, CF₃, Cl)—O—⟨⟩—NH—CO—N(CH₃)₂ | 130 |
| 8 | CF₃—⟨⟩—O—⟨⟩—NH—CO—N(CH₃)₂ | 118 |

EXAMPLE 9

(Process variant (b)) — Preparation of N,N-dimethyl-N'-[4-(2-chloro-4-trifluoromethyl-phenoxy)-phenyl]-urea

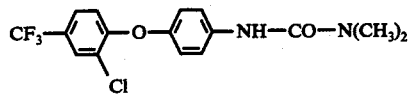 (9)

13 g (0.14 mole) of dimethylcarbamic acid chloride were added dropwise to 29 g (0.1 mole) of 4-(2-chloro-4-trifluoromethyl-phenoxy)-aniline, dissolved in 50 ml of pyridine, at 0° C. The mixture was warmed to 70°–75° C for half an hour, the bulk of the pyridine was stripped off in vacuo and the residue was poured into water and acidified with dilute hydrochloric acid. The precipitate was filtered off, dried and recrystallized from toluene. 29 g (89% of theory) of N,N-dimethyl-N'-[4-(2-chloro-4-trifluoromethylphenoxy)-phenyl]-urea were obtained as pink crystals of melting point 140° C.

EXAMPLE 10

(Process variant (c)) — Preparation of N-methyl-N'-[3-chloro-4-(3-trifluoromethylphenoxy)-phenyl]-urea

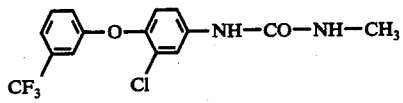 (10)

18.7 g (0.06 mole) of 3-chloro-4-(3-trifluoromethylphenoxy)-aniline were dissolved in 100 ml of acetonitrile, and 3 drops of triethylamine and 4.3 g (0.078 mole) of methylisocyanate were added at 10° C. The mixture was stirred for a further 4 hours at room temperature and then poured into water, and when the reaction mixture had crystallized throughout the solid was filtered off and recrystallized from toluene. 6 g (29% of theory) of N-methyl-N'-[3-chloro-4-(3-trifluoromethylphenoxy)-phenyl]-urea of melting point 160° C were obtained.

The following compounds were obtained analogously to Example 10 in accordance with Process variant (c):

| Ex. No. | Structural formula | Melting point (° C) |
|---|---|---|
| 11 | ⌬-O-⌬-NH-CO-NH-CH₃ (with CF₃) | 119 |
| 12 | Cl-⌬(CF₃)-O-⌬-NH-CO-NH-CH₃ | 173 |
| 13 | Cl-⌬(CF₃)(Cl)-O-⌬-NH-CO-NH-CH₃ | 217 |
| 14 | CF₃-⌬(Cl)-O-⌬(Cl)-NH-CO-NH-CH₃ | 188 |
| 15 | CF₃-⌬(Cl)-O-⌬(Cl,Cl)-NH-CO-NH-CH₃ | 230 |
| 16 | CF₃-⌬-O-⌬-NH-CO-NH-CH₃ | 155 |

The preparation of the intermediates were carried out, for example, as follows:

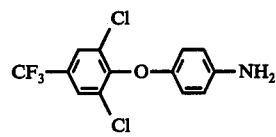

32.5 g of potassium hydroxide flakes in 30 ml of water were added to 54.5 g (0.5 mole) of 4-aminophenol dissolved in 350 ml of dimethylsulfoxide, and 150 ml of a water/dimethylsulfoxide mixture were distilled off in vacuo at 15–20 mm Hg. 125 g (0.5 mole) of 1-trifluoromethyl-3,4,5-trichlorobenzene [$n_D^{20}$: 1.5008 67–68% of theory, compare J. Am. Chem. Soc. 57, 2066–2068 (1935) and U.S. Pat. No. 2,654,789] were then added to the reaction mixture at about 70°–80° C and the mixture was stirred for a further 2 hours at 120°–130° C. The substance was precipitated with water, filtered off, washed with water and recrystallized moist from an ethanol/water mixture, thus giving 40–50% of theory of 4-(2,6-dichloro-4-trifluoromethylphenoxy)-aniline of melting point 128°–130° C.

The following intermediates were prepared analogously:

| Structural formula | Physical data (melting point, refractive index) |
|---|---|
| ⌬(CF₃)-O-⌬-NH₂·HCl | 205–210° C (from water) |
| Cl-⌬(CF₃)-O-⌬-NH₂ | 131–136° C |
| Cl-⌬(CF₃)(Cl)-O-⌬-NH₂·HCl | 220° C |

-continued

| Structural formula | Physical data (melting point, refractive index) |
|---|---|
| CF₃—(Cl,Cl-phenyl)—O—(phenyl)—NH₂ | 200–210° C (from ethanol) |
| CF₃—(Cl,Cl-phenyl)—O—(Cl,Cl-phenyl)—NH₂ | 205–215° C (from 50% strength ethanol) |
| (CF₃-phenyl)—O—(Cl-phenyl)—NH₂ | 74–76° C (from cyclohexane) |
| CF₃—(phenyl)—O—(phenyl)—NH₂ | 76–77° C (via the hydrochloride, from ethanol) |

The active compounds according to the invention have a very good herbicidal activity and can therefore be used for combating weeds.

Weeds in the broadest sense are to be understood as all plants which grow in locations where they are not desired.

Relevant weeds are, in particular: dicotyledons, such as mustard (Sinapis), cress (Lepidium), cleavers (Galium), chickweed (Stellaria), camomile (Matricaria), gallant soldier (Galinsoga), goosefoot (Chenopodium), annual nettle (Urtica), knotgrass (Polygonum), groundsel (Senecio) and rough-haired amaranth (*Amaranthus retroflexus*); monocotyledons, such as timothy (Phleum), bluegrass (Poa), fescue (Festuca), goosegrass (Eleusine), foxtail millet (Setaria), ryegrass (Lolium), cheat (Bromus), barnyard grass (Echinochloa), wild oats (Avena fatua), slender foxtail (Alopecurus) and Johnson grass (*Sorghum halepense*).

Some of the active compounds according to the invention are particularly suitable for the selective combating of weeds, for example in carrots.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds of this invention may be present in the formulations in admixture with other active compounds.

The formulations in general contain from 0.1 to 95 percent by weight of active compounds, preferably from 0.5 to 90 percent by weight.

The active compounds can be used as such or in the form of their formulations or as the use forms prepared therefrom, such as ready-to-use solutions, emulstions, suspensions, powders, pastes and granules. They may be used in the customary manner, for example by spraying, atomizing, dusting, scattering and watering.

The active compounds according to the invention can be employed both in the pre-emergence process and in the post-emergence process. Preferably, they are employed in the post-emergence process.

The amount of active compound employed can be varied within fairly wide ranges. It depends essentially on the nature of the desired effect. In general, the amounts used are between 0.1 and 25 kg/hectare, preferably between 0.3 and 10 kg/hectare.

The active compounds according to the invention in part also display a fungicidal activity. They are, in particular, active against rust diseases; thus, for example, it is possible to treat shoots to protect them against *Puccinia triticina*.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing an active ingredient a compound of the present invention in admixture with a diluent or carrier.

The present invention further provides means of yielding crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the present compounds is illustrated by the following biotest Example, in which the active compounds of this invention are each identified by the number of the corresponding preparative Example hereinafter.

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5-15 cm were sprayed with the preparation of the active compound in such a way as to apply the amounts of active compound per unit area which are indicated in the table.

Depending on the concentration of the spray liquor, the amount of water used was between 1,000 and 2,000 l/ha. After three weeks, the degree of damage to the plants was rated in % damage in comparison to the development of the untreated control. The figures denote:

0% = untreated control
100% = total destruction.

The active compounds, the amounts applied and the results can be seen from the table which follows:

Table A

| Active compound | Amount of active compound used, kg/ha | Chenopodium album | Poa annua | Polygonum spec. | Urtica urens | Portulaca spec. | Digitaria spec. | Carrots | Cotton |
|---|---|---|---|---|---|---|---|---|---|
| Chloroxuron (known) | 4 | 80 | 40 | 80 | 0 | 60 | 40 | 20 | 60 |
|  | 2 | 80 | 20 | 40 | 0 | 40 | 20 | 20 | 40 |
| (9) | 4 | 100 | 100 | 100 | 100 | 100 | 100 | 20 | 40 |
|  | 2 | 100 | 80 | 80 | 60 | 80 | 100 | 20 | 40 |
| (10) | 4 | 100 | 80 | 100 | 80 | 80 | 100 | 20 | 20 |
|  | 2 | 100 | 80 | 100 | 60 | 60 | 80 | 20 | 20 |
| (1) | 4 | 100 | 80 | 100 | 80 | 100 | 100 | 0 | 20 |
|  | 2 | 100 | 60 | 100 | 60 | 80 | 80 | 0 | 20 |
| (7) | 4 | 100 | 100 | 80 | 100 | 100 | 100 | 20 | 40 |
|  | 2 | 100 | 80 | 80 | 100 | 100 | 100 | 20 | 40 |
| (8) | 4 | 100 | 100 | 100 | 100 | 100 | 100 | 20 | 60 |
|  | 2 | 100 | 100 | 100 | 100 | 100 | 100 | 20 | 40 |

The comparative compound "Chloroxuron" in Table A has the formula:

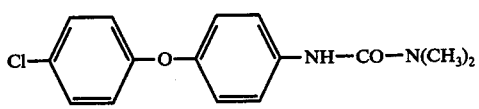

It will be appreciated that the instant specification and examples are set forth by way of illustration and not limitation, and that various modifications and changes may be made without departing from the spirit and scope of the present invention. What is claimed is:

1. (Trifluoromethylphenoxy)-phenylurea compound of the formula:

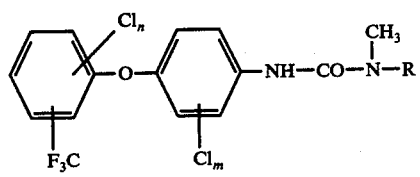

wherein
R is hydrogen or methyl and
n and m are individually selected from integers from 0 to 4 with the proviso that only one of n and m be 0 if the trifluoromethyl group is in the 3-position.

2. (Trifluoromethylphenoxy)-phenylurea compound as claimed in claim 1 wherein R is hydrogen.

3. (Trifluoromethylphenoxy)-phenylurea compound as claimed in claim 1 wherein R is methyl.

4. (Trifluoromethylphenoxy)-phenylurea compound as claimed in claim 1 wherein n is 0 and m is other than 0.

5. (Trifluoromethylphenoxy)-phenylurea compound as claimed in claim 1 wherein m is 0 and n is other than 0.

6. (Trifluoromethylphenoxy)-phenylurea compound as claimed in claim 4 wherein the trifluoromethyl group is in the 3-position.

7. (Trifluoromethylphenoxy)-phenylurea compound as claimed in claim 5 wherein the trifluoromethyl group is in the 3-position.

8. (Trifluoromethylphenoxy)-phenylurea compound as claimed in claim 1 wherein n is 0.

9. (Trifluoromethylphenoxy)-phenylurea compound as claimed in claim 1 wherein n is 1.

10. (Trifluoromethylphenoxy)-phenylurea compound as claimed in claim 1 wherein n is 2.

11. (Trifluoromethylphenoxy)-phenylurea compound as claimed in claim 1 wherein m is 0.

12. (Trifluoromethylphenoxy)-phenylurea compound as claimed in claim 1 wherein m is 1.

13. (Trifluoromethylphenoxy)-phenylurea compound as claimed in claim 1 designated N,N-dimethyl-N'-[3-chloro-4-(3-trifluoromethyl-phenoxy)-phenyl]-urea.

14. (Trifluoromethylphenoxy)-phenylurea compound as claimed in claim 1 designated N,N-dimethyl-N'-[4-(2,4-dichloro-6-trifluoromethylphenoxy)-phenyl]-urea.

15. (Trifluoromethylphenoxy)-phenylurea compound as claimed in claim 1 designated N,N-dimethyl-N'-[4-(4-trifluoromethylphenoxy)-phenyl]-urea.

16. (Trifluoromethylphenoxy)-phenylurea compound as claimed in claim 1 designated N,N-dimethyl-N'-[4-(2-chloro-4-trifluoromethylphenoxy)-phenyl]-urea.

17. Herbicidal composition comprising an agriculturally acceptable inert carrier and, in effective amounts, a (trifluoromethylphenoxy)-phenylurea compound as claimed in claim 1.

18. Method of combatting undesired vegetation which method comprises applying to the locus of such vegetation effective amounts of a (trifluoromethylphenoxy)-phenylurea compound of the formula:

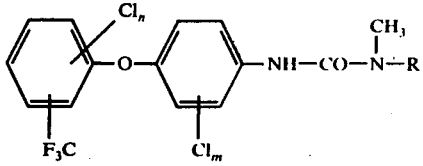

wherein

R is hydrogen or methyl and n and m are individually selected from integers from 0 to 4 with the proviso that only one of n and m be 0 if the trifluoromethyl group is in the 3-position.

19. Method as claimed in claim 18 wherein said compound is selected from the group consisting of:
N,N-dimethyl-N'-[3-chloro-4-(3-trifluoromethyphenoxy)-phenyl]-urea;
N,N-dimethyl-N'-[4-(2,4-dichloro-6-trifluoromethylphenoxy)-phenyl]-urea;
N,N-dimethyl-N'-[4-(4-trifluoromethylphenoxy)-phenyl]-urea; and
N,N-dimethyl-N'-[4-(2-chloro-4-trifluoromethylphenoxy)-phenyl]-urea.

20. Method as claimed in claim 18 wherein said compound is applied in an amount from 0.1 to 25 kg. per hectare.

21. A method for combating undesired vegetation comprising at least one weed of the group *Chenopodium album, Poa annua, Polygonum, Urtica urens,* Portulaca and Digitaria after emergence in a field of carrots or cotton which comprises applying to the locus of such weeds an amount from 2 to 4 kg per hectare of a compound of the formula

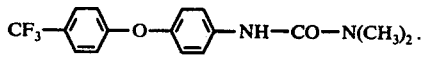

* * * * *